(12) United States Patent
Dobson et al.

(10) Patent No.: US 8,706,431 B2
(45) Date of Patent: Apr. 22, 2014

(54) DIRECT SEQUENCE SPREAD SPECTRUM PREDICTIVE CABLE AND COMPONENT FAILURE TECHNOLOGY

(75) Inventors: W. Kurt Dobson, Midvale, UT (US); Gill Bearnson, Salt Lake City, UT (US)

(73) Assignee: World Heart Corporation, Salt Lake City, UT (US)

( * ) Notice: Subject to any disclaimer, the term of this patent is extended or adjusted under 35 U.S.C. 154(b) by 499 days.

(21) Appl. No.: 12/820,884

(22) Filed: Jun. 22, 2010

(65) Prior Publication Data

US 2011/0313691 A1 Dec. 22, 2011

(51) Int. Cl.
*G01R 31/00* (2006.01)

(52) U.S. Cl.
USPC .......................................................... 702/58

(58) Field of Classification Search
USPC .......................................................... 702/58
See application file for complete search history.

(56) References Cited

U.S. PATENT DOCUMENTS

| | | | |
|---|---|---|---|
| 7,165,200 B2 * | 1/2007 | Jani et al. ..................... | 714/724 |
| 7,403,559 B1 | 7/2008 | Fisher et al. | |
| 7,548,071 B2 * | 6/2009 | Harrison et al. ............. | 324/617 |
| 2006/0012376 A1 | 1/2006 | Furse et al. | |
| 2007/0194796 A1 | 8/2007 | Harrison et al. | |

FOREIGN PATENT DOCUMENTS

WO 2005109020 A2 11/2005

OTHER PUBLICATIONS

Partial International Search Report for PCT/US2011/041282 mailed Oct. 25, 2011.
Tam, Wai M. et al., "Generalized Correlation-Delay-Shift-Keying Scheme for Noncoherent Chaos-Based Communication Systems," ISCAS 2004, pp. 601-604, May 23, 2004.
"Universal Approximation Theorem", retrieved from http://en.wikipedia.org/wiki/Universal_approximation_theorem on Jun. 3, 2010, 2 pages.
"Wavelet", retrieved from http://en.wikipedia.org/wiki/Wavelet on Jun. 3, 2010, 12 pages.

* cited by examiner

*Primary Examiner* — Aditya Bhat
(74) *Attorney, Agent, or Firm* — Lerner, David, Littenberg, Krumholz & Mentlik, LLP

(57) ABSTRACT

There are disclosed systems and methods of determining a fault location on a wire. In an embodiment, a system includes a PN code having a chip-time. Software code is provided for delaying the PN code a series of delays to form delayed PN samples, a sum of the series of delays being less than one chip-time. Software code is provided for summing the delayed PN samples with the PN code to form a summed sequence. Software code is provided for transmitting the summed PN sequence to the wire. Software code is provided for receiving a signal from the wire related to the summed PN sequence. Software code is provided for mixing the signal received from the wire with a delayed copy of the summed PN sequence so as to form a mixed signal. Software code is provided for integrating the mixed signal to map faults. Other embodiments are also disclosed.

16 Claims, 11 Drawing Sheets

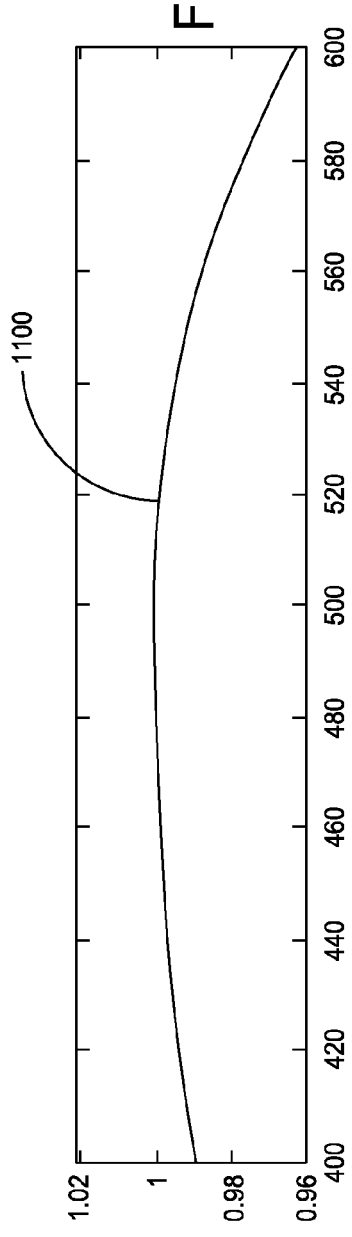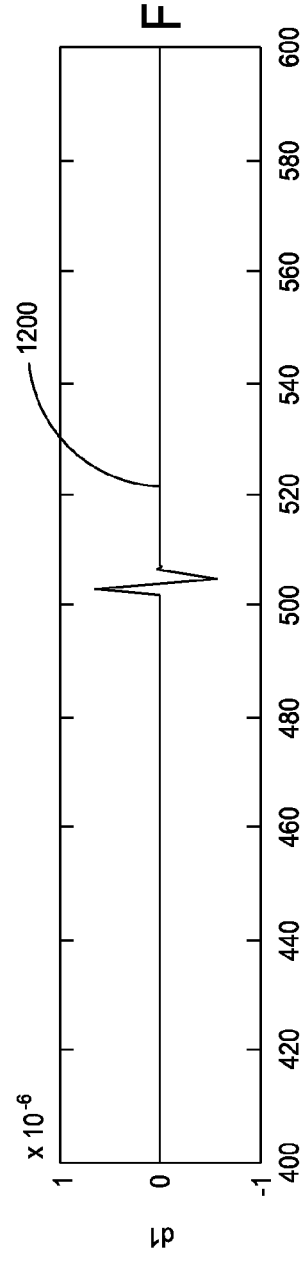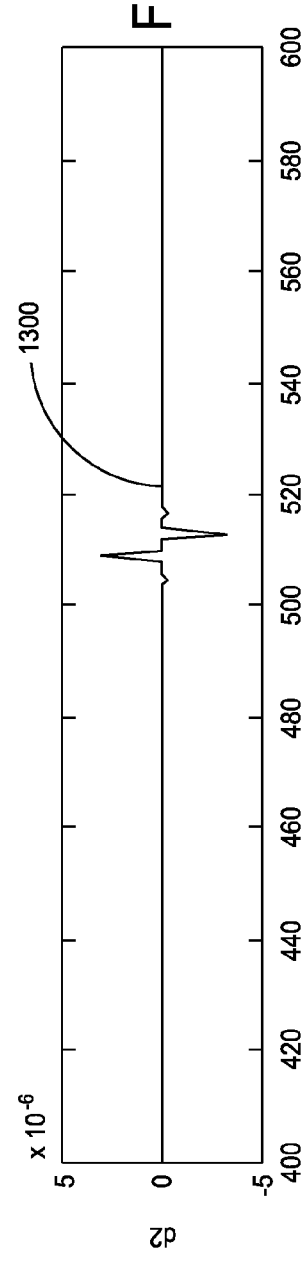

DIRECT SEQUENCE SPREAD SPECTRUM PREDICTIVE CABLE AND COMPONENT FAILURE TECHNOLOGY

BACKGROUND

Prior spread spectrum systems have been developed that allow testing of live wires where a direct sequence spread spectrum signal at noise levels is added to the existing signal, transmitted down the wire, and a reflected signal is delayed by time. The reflected signal correlated to determine the characteristics and fault location of the wires. These systems perform poorly when the chip time of the spread spectrum signal (Tc) is less than the round-trip time for signals to travel over the wire (Tw).

For many applications, the constraint that Tc<Tw is not an issue. For example, one of the most interesting and useful applications has been for testing aging aircraft wiring where wire lengths are normally 10's to hundreds of feet in length.

However, there are many applications, particularly in life-critical medical devices such as defibrillators, pace-makers, and artificial heart pumps where the wires are very short (inches to a few feet), and are the least reliable component of the system. A method of testing these short wires in situ, capable of providing early prediction of failure would be of great benefit.

Prior art configurations requiring that Tc<Tw cannot address these applications. In fact, prior art cannot find a fault in a wire nearer than one chip time, or approximately 1*Tc+Tsc, where Tsc is the sub-chip time.

SUMMARY OF THE INVENTION

In an embodiment, there is provided a system for determining a fault location on a wire, the system comprising a PN code having a chip-time; software code for delaying the PN code a series of delays to form delayed PN samples, a sum of the series of delays being less than one chip-time; software code for summing the delayed PN samples with the PN code to form a summed sequence; software code for transmitting the summed PN sequence to the wire; software code for receiving a signal from the wire related to the summed PN sequence; software code for mixing the signal received from the wire with a delayed copy of the summed PN sequence so as to form a mixed signal; and software code for integrating the mixed signal to map faults so as to detect indications of failures.

In another embodiment, there is provided a method of determining a fault location on a wire, the method comprising providing a PN code having a chip-time; delaying the PN code a series of delays to form delayed PN samples, a sum of the series of delays being less than one chip-time; summing the delayed PN samples with the PN code to form a summed sequence; transmitting the summed PN sequence to the wire; receiving a signal from the wire related to the summed PN sequence; mixing the signal received from the wire with a delayed copy of the summed PN sequence so as to form a mixed signal; and integrating the mixed signal to map faults so as to detect indications of failures.

Other embodiments are also disclosed.

BRIEF DESCRIPTION OF THE DRAWINGS

Illustrative embodiments of the invention are illustrated in the drawings, in which:

FIGS. 11-13 include plots showing the detection of a discontinuity in one of a signal's derivatives through wavelet analysis.

DETAILED DESCRIPTION

A large body of work exists describing time-domain reflectometry (TDR), frequency-domain reflectometry (FDR), standing wave reflectometry (SWR), and more recently spread-spectrum time domain reflectometry (SSTDR). Of these methods only a few are suitable to allow cable testing at the same time live signals are present on the wiring. This is accomplished through the use of pseudo-random (PN) spreading codes as the test signal applied to the wire below the noise floor of the live signal. The spread spectrum signal is recovered from the noise due to the processing gain (length of the code) by correlating the signal against the known PN code.

Figure 1:
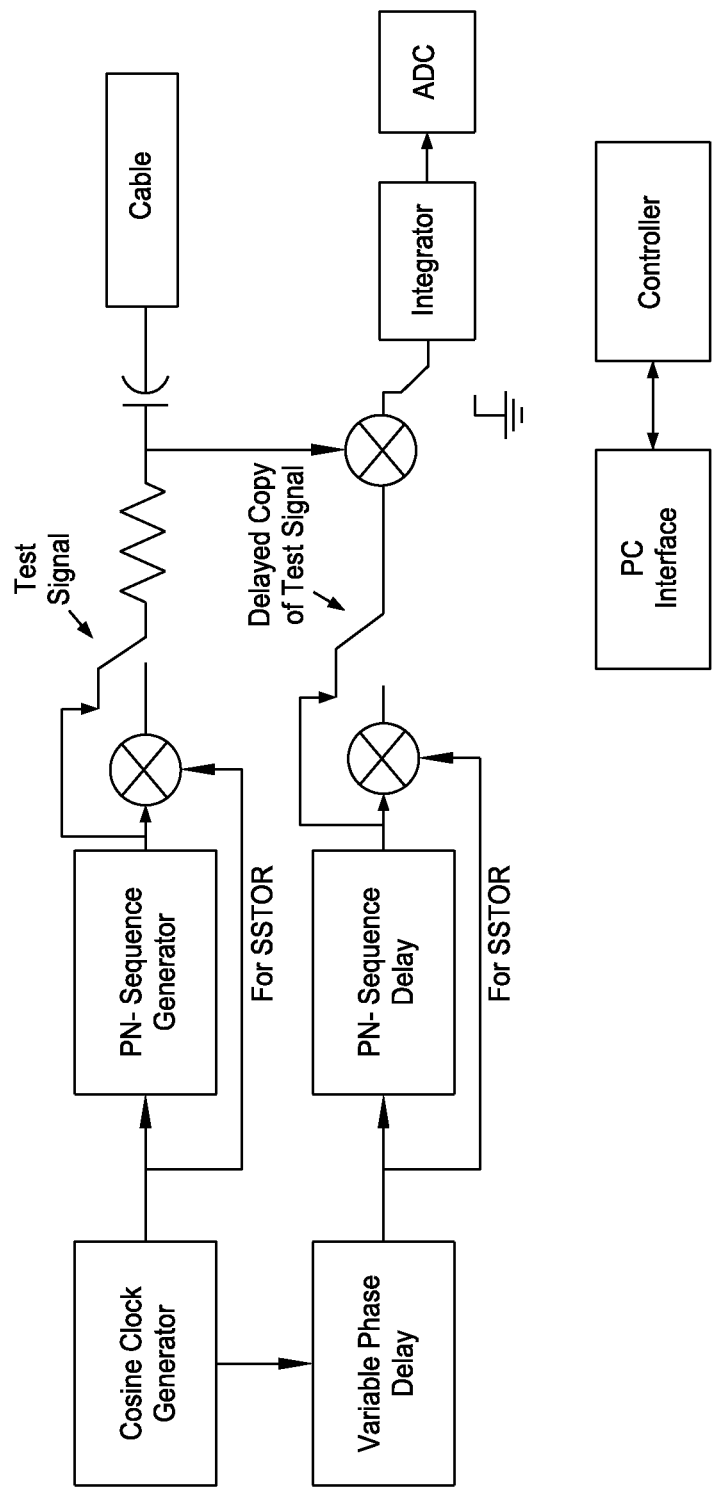
FIG. 1 illustrates an embodiment of determining the characteristics and fault location of wires.

SSTDR systems have been described by that allow testing of live wires where a direct sequence spread spectrum signal at noise levels is added to the existing signal and transmitted down the wire and a reflected signal is delayed by time and correlated to determine the characteristics and fault location of the wires. The block diagram of FIG. 1 illustrates an embodiment of determining the characteristics and fault location of wires.

Figure 2:
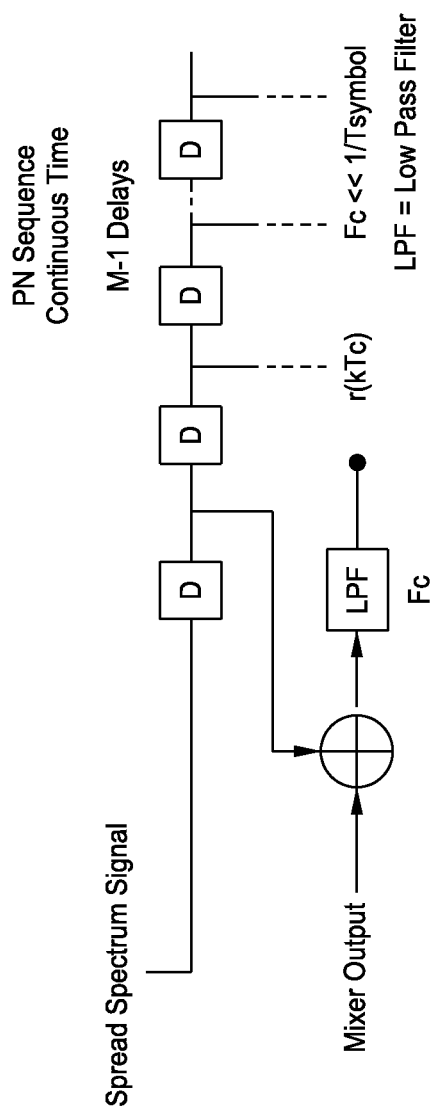
FIG. 2 is a block diagram illustrating at least one-chip delay (Tc) added to the PN sequence prior to correlation and integration.

The variable phase delay block consists of integer spread spectrum chip delays (Tc), plus sub-chip delays (Tsc). The block diagram shown in FIG. 2 reveals the fact that at least one-chip delay (Tc) is added to the PN sequence prior to correlation and integration. If Tc is zero, plus any Tsc<Tc, the output of the integrator will be the entire autocorrelation of the PN sequence, precluding detection of a reflected (e.g., fault) signal. This configuration makes it difficult or impossible to achieve high sensitivity during the first chip time.

Generally, this configuration uses the notation of Tb as the bit time of the live signal, Tc to denote the time of each spread spectrum chip, and Tw as the round-trip time for a signal to propagate down the wire and back. The general requirement for this prior art system is that Tb>Tc<Tw. Since this is a spread spectrum method, the requirement for Tb>Tc is reasonable.

For many applications, the constraint that Tc<Tw is not an issue. For example, one of the most interesting and useful applications has been for testing aging aircraft wiring where wire lengths are normally tens to hundreds of feet in length. Therefore, choosing a feasible spread spectrum Tc of 10 nanoseconds (100 Mhz), simply means that a fault cannot be found that is closer than approximately 5 feet due to Tw (assuming the signal travels at the speed of light, C), but that faults can be found 5 feet or farther away with a resolution of Tsc. In practice, signals traveling over wires travel at some large fraction of C which is determined by the relative dielectric constant, er of the wire.

However, there are many applications, particularly in life-critical medical devices such as defibrillators, pace-makers, and artificial heart pumps where the wires are very short (e.g., inches to a few feet), and are the least reliable component of the system. A method of testing these short wires in situ, capable of providing early prediction of failure would be of great benefit.

Prior art configurations that require that Tc<Tw have serious performance issues. This is due to the entire correlation value is present, making the (SNR) of the full correlation versus the very small signal very difficult to detect.

However, there is another solution to these problems to allow fault detection on short wires with high resolution of fault location and high sensitivity to wire nicks, chaffing and degradation so as to allow advance prediction of failure.

Understanding Impedance, Attenuation, Reflections and Echoes

It is important to understand the mathematical representation of signals on wires. In a perfectly matched system, where the source impedance is the same as the load impedance, no signal reflections occur. In practice however, there are always slight changes in impedance due to connectors, imperfections in insulation, and the reality that impedance is never the same over frequency. Since the present method uses a spread spectrum technique wherein the frequency is broad, these effects are important to understand as a function of both time and frequency.

In an embodiment, slight anomalies in impedance may be used to detect changes or faults in wiring and wired system components. These slight anomalies may be due to, but are not limited to, a nick in the wire insulation, chaffing, strain or breaking of a wire strand. Any change in impedance at some frequency will cause multiple reflections (echoes) to occur, and attenuation and phase distortion of the signal over frequency.

Figure 3:
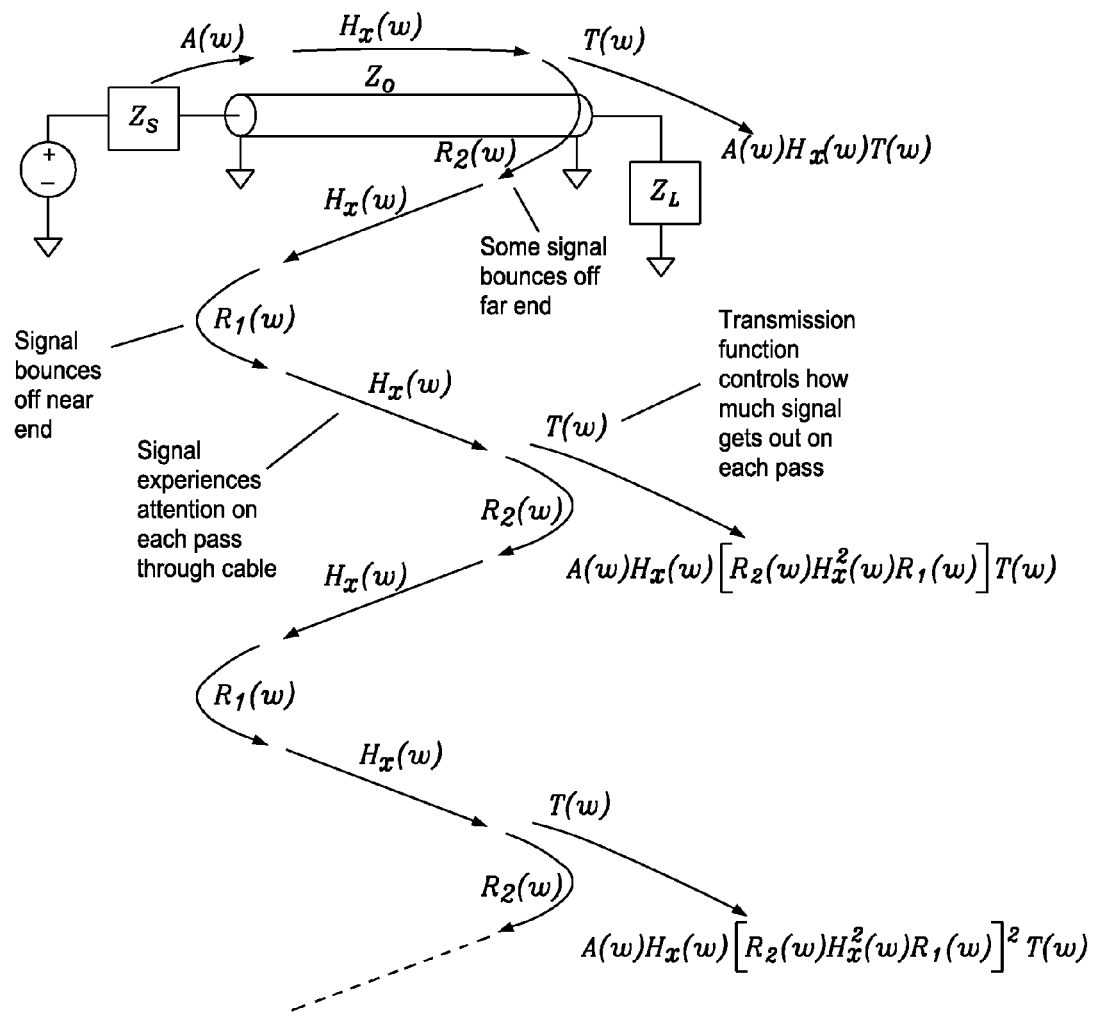
FIG. 3 an embodiment of determining the characteristics and fault location of wires.

Referring to FIG. 3, when a signal is impressed on the end of a transmission line, a fraction of the full source voltage propagates down the line. This fraction is a function of frequency which may be referred to as A(w), the input acceptance function. The value of A(w) is determined by the source impedance Zs, the transmission line impedance as defined above, and the input acceptance equation of:

$$A(w) := \frac{Zo(w)}{Zs(w) + Zo(w)}$$

As the signal propagates, it is attenuated by the propagation function Hx(w), except that due to the skin effect, the R(w) term is now a function of frequency.

$$Hx(w,X) := e^{-X \cdot \sqrt{(R(w)+j \cdot w \cdot L)(j \cdot w \cdot C)}}$$

At the far end of the cable, a fraction of the attenuated signal emerges. This fraction is also a function of frequency which may be referred to as T(w), the output transmission function. The value of T(w) is determined by the load impedance Z1, the transmission line impedance, and the output transmission function. T(w) ranges from 0 to 2.

$$T(w) := \frac{2 \cdot Z1(w)}{Z1(w) + Zo(w)}$$

When this fraction T(w) of the propagating signal emerges from the far end, a reflected signal also travels back along the cable towards its source. As it reflects, it crosses over the tail of the incoming signals. Both signals propagate simultaneously in opposite directions, neither interfering with the other. The fraction of the propagating signal that reflects back towards the source which may be referred to as R2(w), the far end reflection:

$$R2(w) := \frac{Z1(w) - Zo(w)}{Z1(w) + Zo(w)}$$

This reflected signal is again attenuated by Hx(w) as it travels back to the head end, where it reflects a second time off the source impedance. The source end reflection is then given by R1(w):

$$R1(w) := \frac{Zs(w) - Zo(w)}{Zs(2) + Zo(w)}$$

After the head-end reflection, the signal is attenuated a third time by Hx(s), and then part of it again emerges through the transmission function T(w). Part of this signal also reflects back toward the source, in an endless cycle.

The first signal to emerge from the cable is attenuated by A(w), H(x), and T(w).

$$S_0(w) = A(w)Hx(w)T(w)$$

The second to emerge after having reflected off both load and source ends is attenuated by:

$$S_1(w) = A(w)H_xw(R2(w)Hx^2(s)R1(w))T(w)$$

Successive emerging signals are characterized by:

$$S_N(w) = A(w)Hx(w)[R2(w)(H_x)^2(s)R_1(w)]^N T(w)$$

Eventually, all signals N=[0, 1 ... ∞] emerge. The sum of all these emerging signals is:

$$s_{inf}(w) = \sum_{n=0}^{inf} s_n(w)$$

Solving the above equation is untenable, but fortunately, there is a closed-form equivalent solution for this infinite sum that gives the frequency response, from source to load of the transmission system shown in FIG. 3.

$$S(\omega, X) := \frac{A(\omega) \cdot Hx(\omega, X) \cdot T(\omega)}{1 - (R2(\omega) \cdot Hz(\omega, X)^2 \cdot R1(\omega))}$$

where ω is radian frequency, and X is the length of the transmission line in inches.

The equation below may be used to convert radian frequency to Hertz:

$$f(\omega) := \frac{1}{2} \cdot \frac{\omega}{\pi}$$

The direct solution to using spread spectrum to achieve high location precision is to use prior art and simply increase the frequency. That is, reduce the chip-time Tc to a very small number. For example, to find a fault within 1 inch, then Tc needs to be 1/12 of approximately 1 nanosecond, or 12 Ghz. This is certainly possible, particularly if a custom semiconductor can be designed to integrate all the functions. Otherwise, a discrete implementation would be large, expensive, and difficult to design and implement. Moreover, most cables that are not RF coaxial cables will severely attenuate these high frequencies.

Therefore, a method is required that keeps the spectrum on the wire within some reasonable attenuation bounds while allowing a high degree of precision in locating faults in the time-domain is required.

Figure 4:
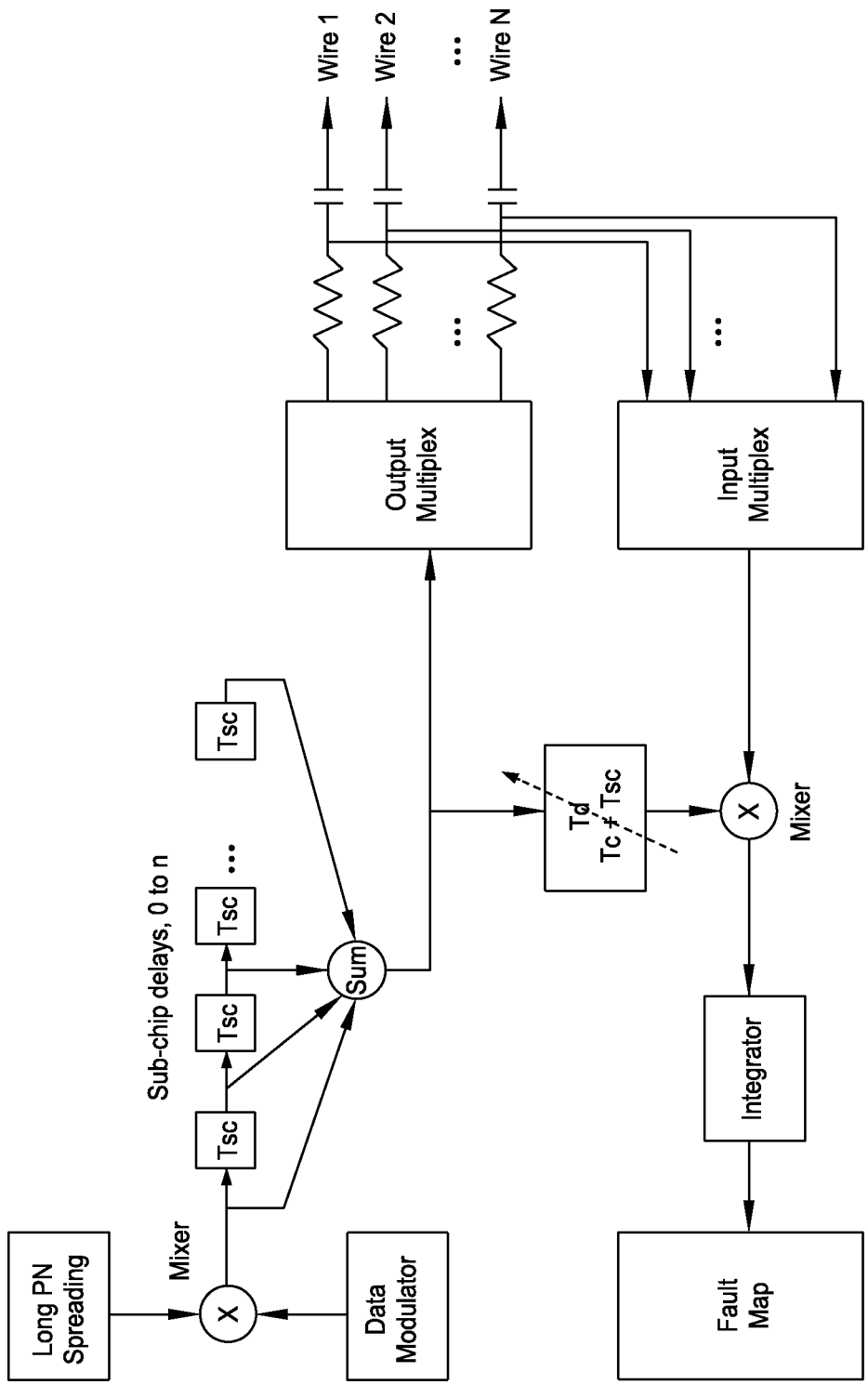
FIG. 4 illustrates a block diagram of one embodiment using a pseudo-random PN code.

A block diagram of one embodiment using a pseudo-random PN code is shown in FIG. 4. In an embodiment, the code is a Maximal Length Sequence (MLS), but may be Gold, Kasami or other codes with their own advantages. MLS codes are unique in that their autocorrelation function is zero outside perfect code alignment. The chip-time Tc is chosen as a system design tradeoff against other constraints, but is generally as high a frequency as possible where attenuation of the cable is not an issue and within hardware feasibility.

The length of the PN code should be longer than the total ringing time of the channel (wire) at some dB determined as the smallest impedance anomaly that is to be detected.

The long PN spreading code is delayed by a series of delays of length Tsc whose value is determined below. The sum of these delay times are less than one PN sample (chip-time or Tc). These delayed PN samples are summed with the original code to form a Summed PN sequence. This time-domain signal is transmitted to one of N wires selected through a multiplexer. A received signal is also selected by a multiplexer and mixed with a delayed copy of the Summed PN sequence and then integrated. Multiple symbols of the entire PN sequence can be transmitted over each wire to obtain whatever system sensitivity is required for the application to detect nicks, abrasions or other indications of early failure.

Under separate control (not shown) a processor would cycle though each wire and send multiple PN symbols at every possible time delay (Td) and obtain the integrated correlation which reveals the fault location.

As an exemplary design, the wires may have to be tested a length of 2 feet and are twisted pairs. Propagation of a signal given the relative dielectric, er, is computed to be 1.6074 nano-seconds per foot. The round trip delay time, Tw, is therefore 6.4298 nano-seconds or approximately 155 Mhz.

If one goal is to be able to detect a fault within an inch, a time resolution of 1.3395e-010, or 133 pico-seconds is required for the signal to travel from the start of the cable one inch, then to return is 268 pico-seconds. The Tsc delay is chosen to be approximately 268 pico-seconds. This can be achieved easily in an FPGA or CPLD using buffers as delay elements.

Next, a clock frequency is chosen to be within the limits of implementation hardware, which in this example will be a field-programmable gate array (an FPGA.) The clock frequency is chosen as 250 Mhz, which results in a Tc of 4 nano-seconds.

Next, the number of Tsc delays is thus Tc/Tsc-=16. Therefore, there will be 16 Tsc delay lines in the implementation. Delays greater than 16*Tsc are implemented by Tc+1.

Deciding on the length of the PN code depends on the required system sensitivity (e.g., how far down an impedance anomaly is to be detected, which relates to processing gain, and the worst case ringing time of the channel.) In practice, the sensitivity will dictate the length of the PN code, and generally, the longer the better, although integration across multiple PN sequences are generally used.

In practice long PN codes will be used. However, to illustrate the way the PN sequence is built and summed using Tcs delay elements, we will use a very short code (length 7).

First, a bipolar MLS sequence of length 7 is used:

This sequence is then upsampled by the number of Tcs delays used. For this example, 4 delays are used rather than 16. Each PN chip is repeated 4 times, resulting in a sequence that is length 28:

[−1 −1 −1 −1 1 1 1 1 −1 −1 −1 −1 −1 −1 −1 −1 −1 −1 −1 −1 1 1 1 1 1 1 1 1]

A matrix is then formed with each row right-shifted 1 Tsc and zero-padded: [−1 −1 −1 −1 1 1 1 1 −1 −1 −1 −1 −1 −1 −1 −1 −1 −1 −1 −1 −1 1 1 1 1 1 1 1 1 0 −1 −1 −1 −1 1 1 1 1 −1 −1 −1 −1 −1 −1 −1 −1 −1 −1 −1 −1 −1 1 1 1 1 1 1 1 1 0 0 −1 −1 −1 −1 1 1 1 1 1 −1 −1 −1 −1 −1 −1 −1 −1 −1 −1 −1 −1 −1 1 1 1 1 1 1 1 1 0 0 0 −1 −1 −1 −1 1 1 1 1 −1 −1 −1 −1 −1 −1 −1 −1 −1 −1 −1 −1 −1 1 1 1 1 1 1 1 1]

The transmit signal is formed by summing each column sum of the matrix, translating several bipolar PN sequences to a signal that has a magnitude of plus/minus the upsample number:

[−1 −2 −3 −4 −2 0 2 4 2 0 −2 −4 −4 −4 −4 −4 −4 −4 −4 −4 −2 0 2 4 4 4 4 4]

Note that this signal never has a change in value of more than 2 between any two samples. This limits the spectrum of the resulting code to the same spectrum of the original bipolar signal.

Figure 5:
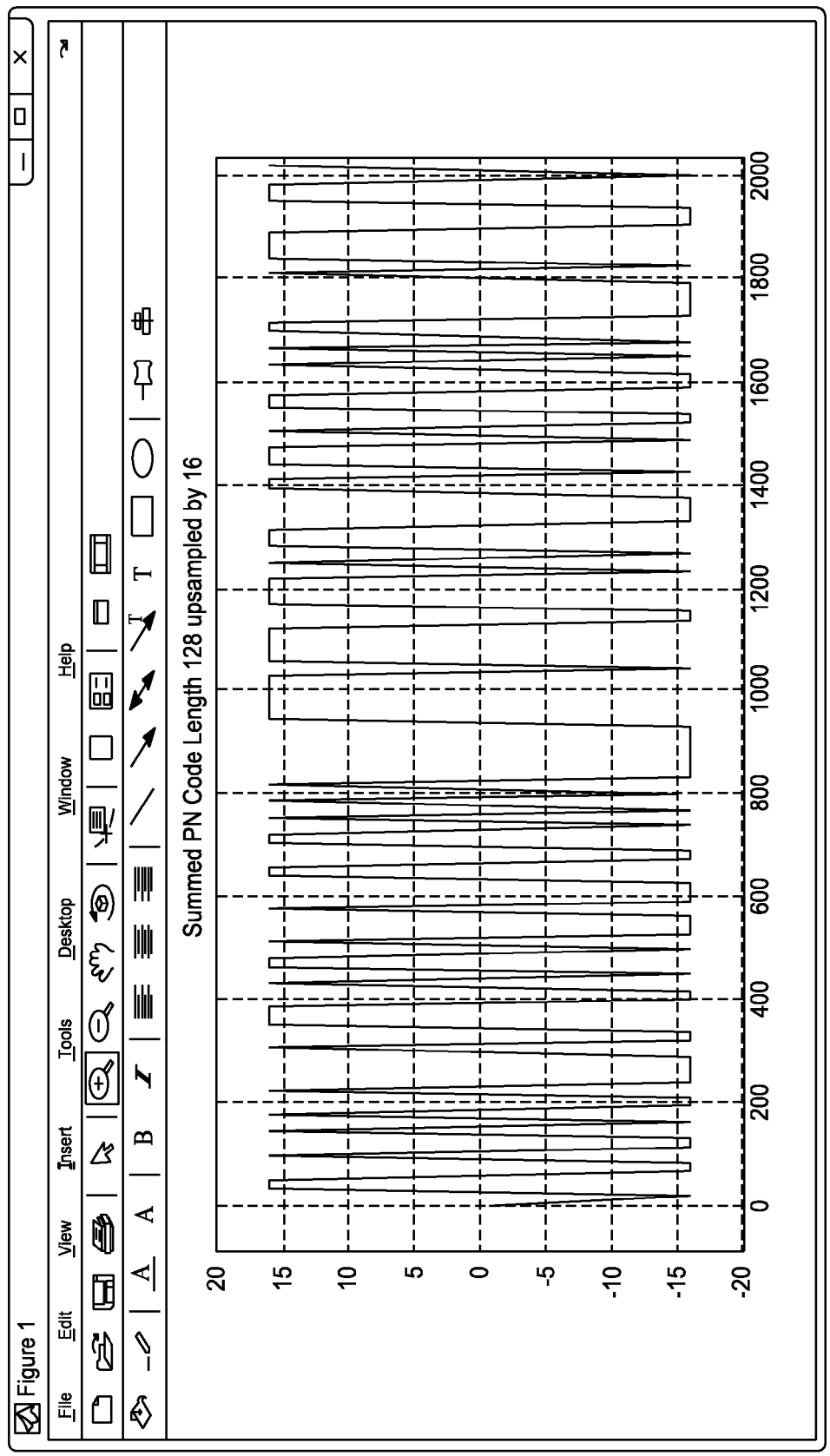
FIG. 5 illustrates a plot of the resulting code in the time domain.

Now, using a more practical code length of 128, and an upsample rate of 16, a plot of the resulting code in the time domain is illustrated in FIG. 5. The resulting summed PN code has a length of 127*16=2032, and a range from −16 to +16 due to the summing.

Figure 6:
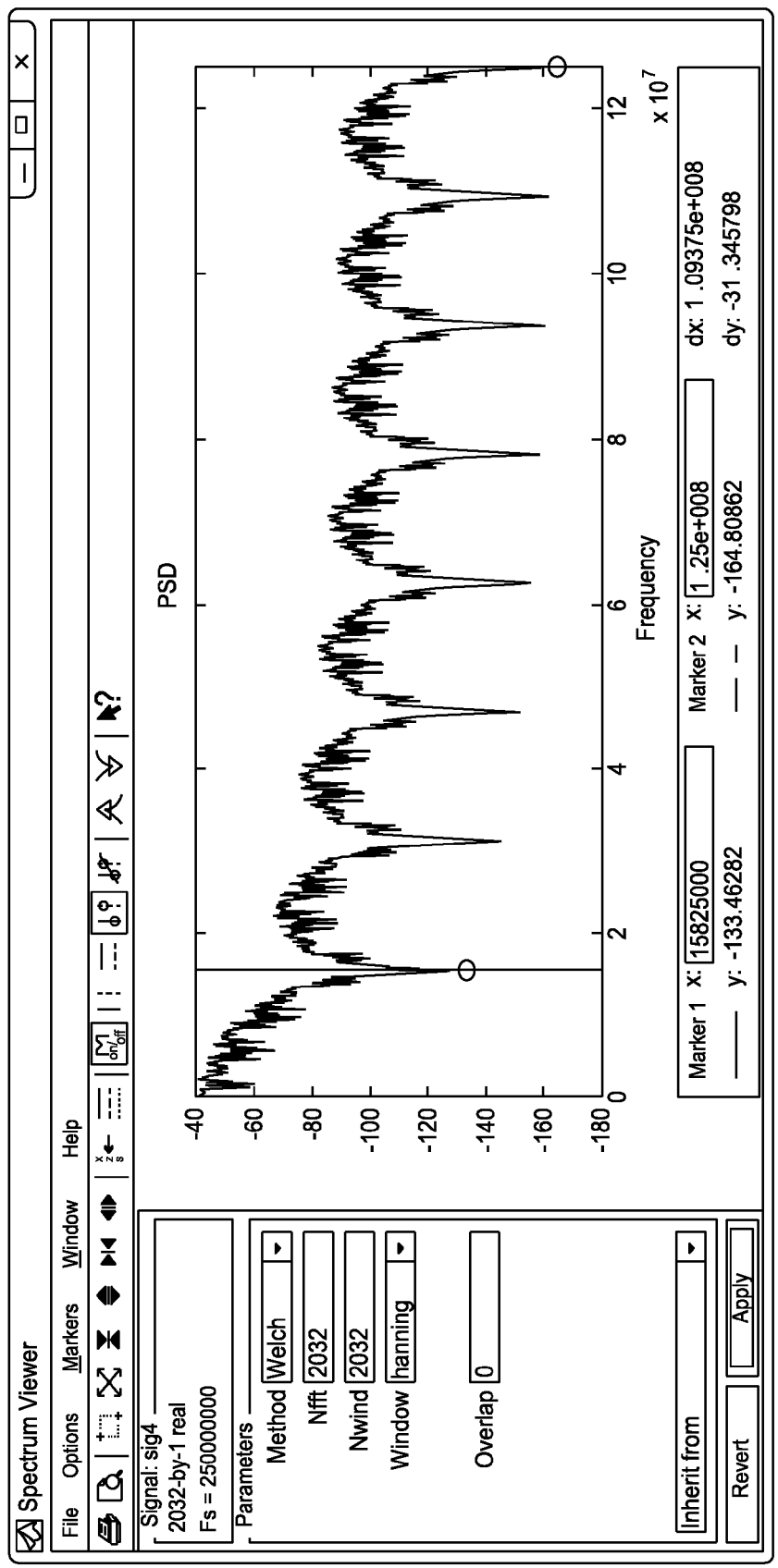
FIG. 6 illustrates a spectral plot of the signal of FIG. 5.

The result using this method of constructing the transmit signal with shifting and summing is a spectrum that is the same as the original PN sequence. If the original PN code were sampled at 250 Mhz and since the code is pseudo random, the spectrum would be randomly distributed between zero and 125 Mhz. FIG. 6 is a spectral plot of the signal of FIG. 5, which shows the energy of the upsampled, shifted and summed signal contained within the same 125 Mhz spectrum.

Figure 7:
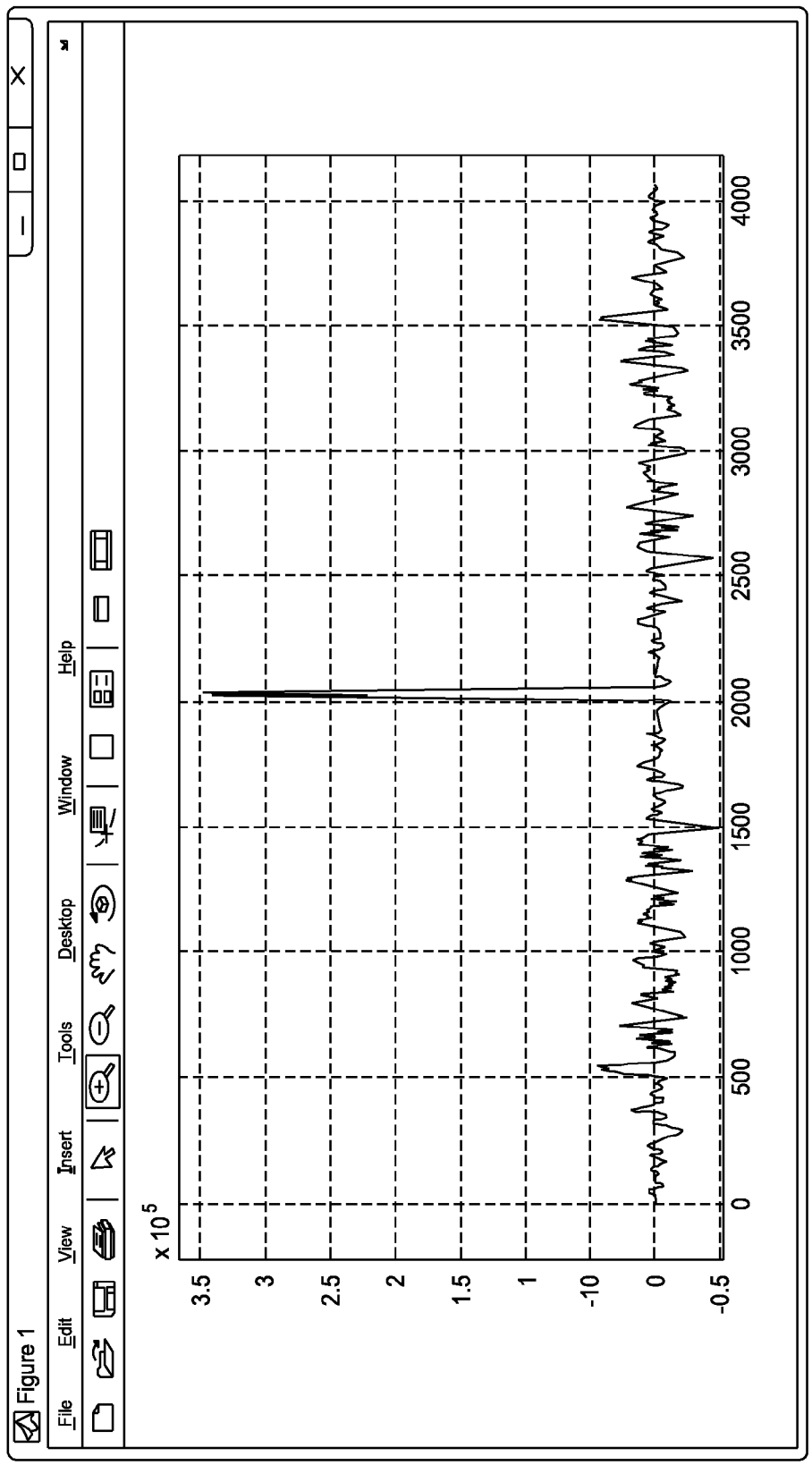
FIG. 7 illustrates a plot of the cross correlation of the PN sequence against itself (i.e., auto-correlation)

The property of the resulting signal that allows detection of defects in the wire is the cross-correlation property. The plot of FIG. 7 shows the cross correlation of the PN sequence against itself (i.e., auto-correlation). Since the sequence is 2032 Tsc chips long, the maximum correlation occurs at step 2032 where both sequences are aligned. The magnitude of the correlation sequence is roughly 346,000, which represents approximately 110 dB of processing gain 20*log 10(346,000).

The cross correlation between two vectors x and y may be computed as:

$$\hat{R}_{xy}(m) = \begin{cases} \sum_{n=0}^{N-m-1} x_{n+m} y_n^* & m \geq 0 \\ \hat{R}_{yx}^*(-m) & m < 0 \end{cases}$$

Figure 8:
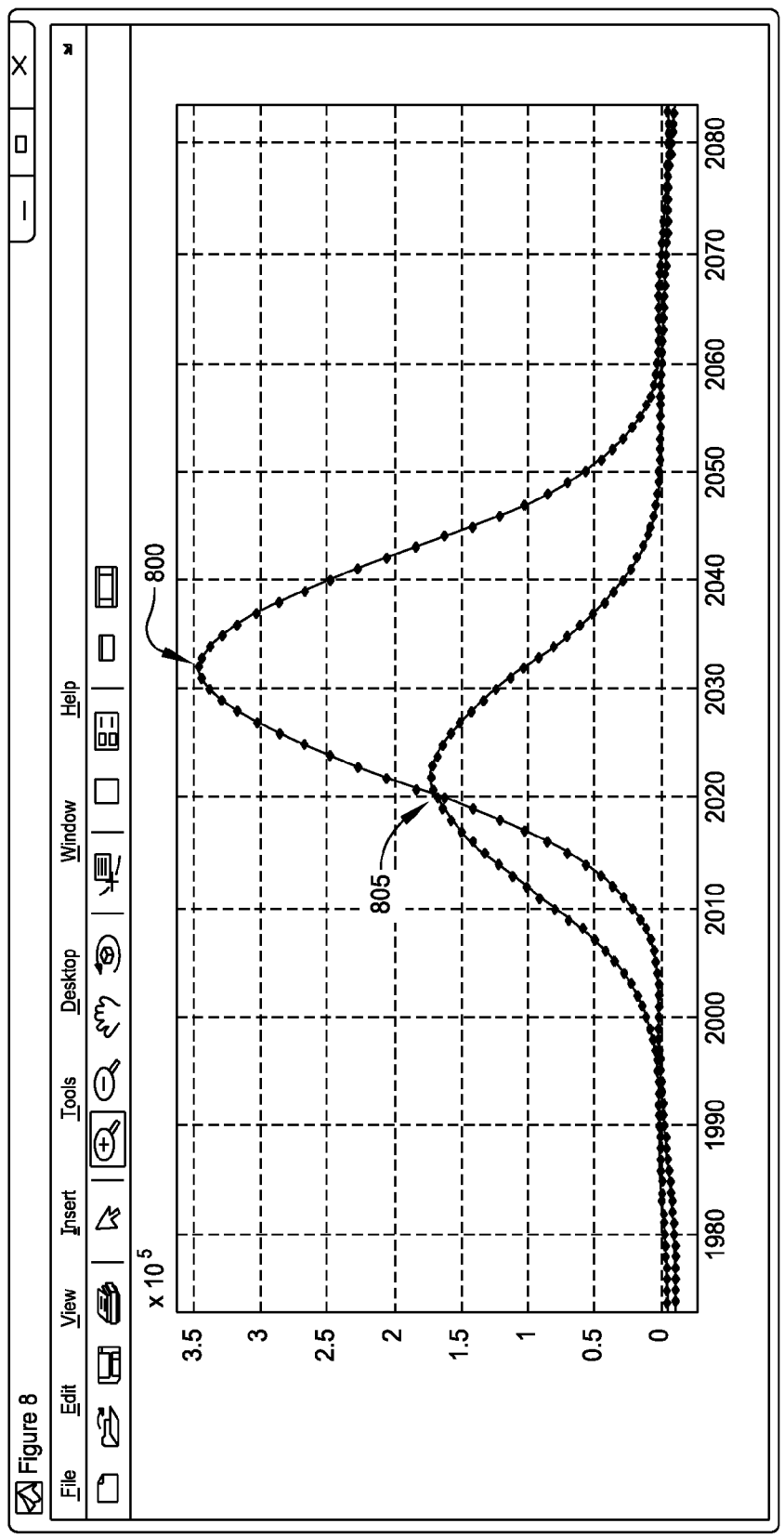
FIG. 8 illustrates the full correlation peak and the partial correlation peak.

To test the detection ability of the resulting PN sequence, a channel model may be constructed with a fault located at 10 Tsc chips away from the point where the signal is injected into the wire at ½ the magnitude of the full correlation. The plot of FIG. 8 shows the full correlation peak 800 and the partial correlation peak 805, which is 10 Tsc sample times away from the blue signal.

Figure 9:
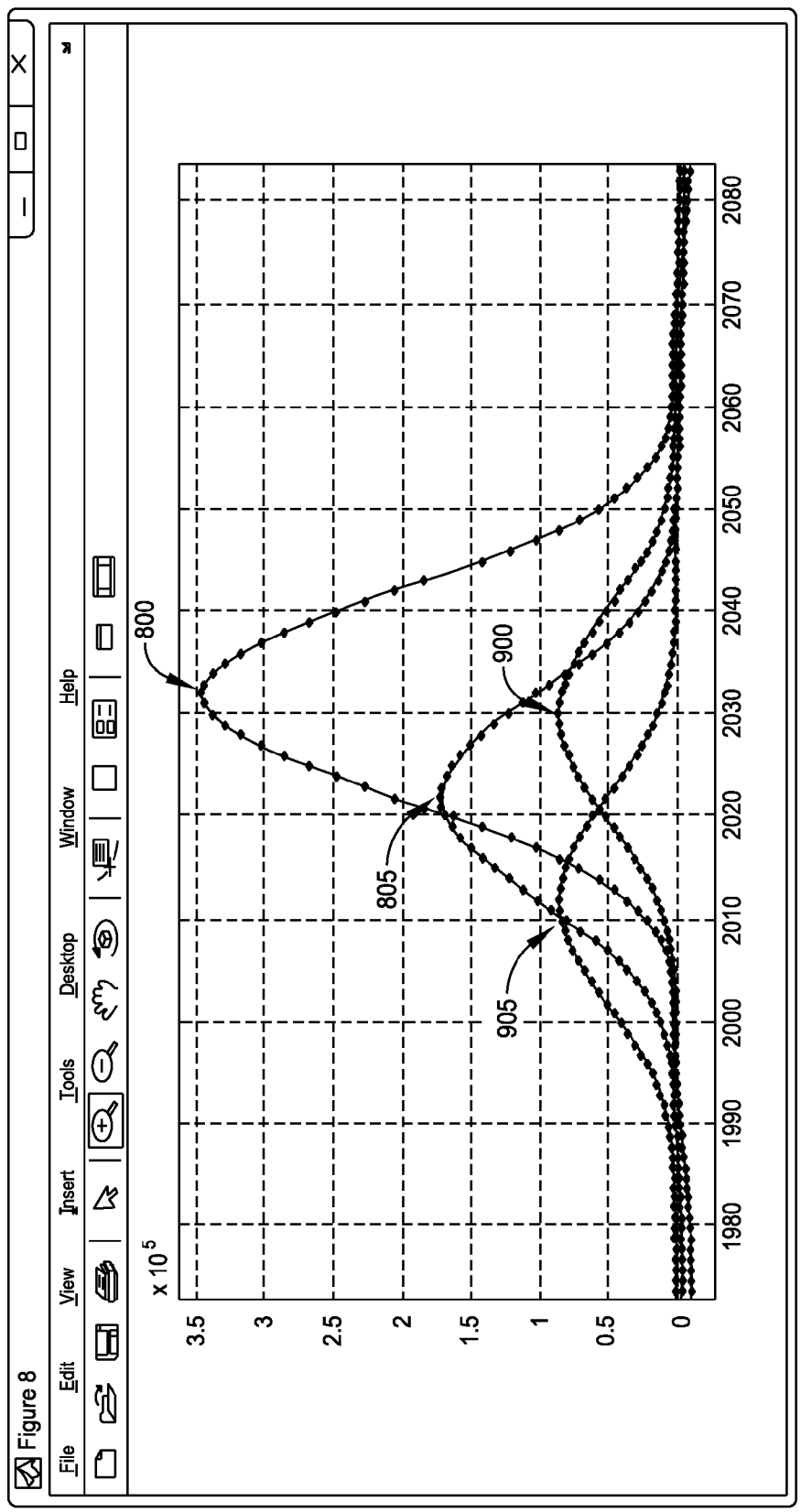
FIG. 9 is a plot illustrating the location of the three faults at 2, 10, and 20 Tsc chips away from the full correlation peak of FIG. 8.

A second fault 900 and third fault 905 may be added to the channel simulation with a fault located 1 and 20 Tsc chips away from the full correlation point at ¼th the peak value. The plot of FIG. 9 shows the location of the three faults at 2, 10, and 20 Tsc chips away from the full correlation peak. This illustrates the algorithms ability to detect multiple faults spaced closely together in the time domain, even though the spectrum of the transmit signal is 1/16th of what would be required for a brute-force approach.

In practice, as many PN symbols can be sent as required to achieve the required sensitivity for the application through integration. Every 10× in symbols will achieve an additional 20 dB of processing gain. Appropriate long PN codes with repeated symbols can be designed to achieve the sensitivity requirement of any system.

A method of spread spectrum time domain reflectometry may be based on a unique method of constructing an upsampled PN sequence without increasing the resulting spectrum of the original sequence. A system simulation that implements the method, which simulates a channel (e.g., wires) with defects has been written and tested with encouraging results.

In an embodiment, there may be provided an in situ cable test technology capable of predicting failure greater than 90 days for all controller cables, connectors, motor and levitation windings for the World Heart Levacor artificial heart pumps. This technology also applies to other medical market segments including defibrillators, pace-makers, and other life critical devices.

Predictive Capability

A novel approach to testing wires may include predictive monitoring. This predictive monitoring approach may include comparing compiled data from known good cables and mechanically stressed cables with test data from a wire under test. In an embodiment, a neural network may be implemented to compare test data from a wire under test with compiled data from known good cables and mechanically stressed cables.

In an embodiment, a diagnostic system may be constructed and trained to recognize cable faults. In an embodiment, the system may include using a physical accelerated cable stress test fixture, data acquisition equipment, and post signal processing methods utilizing wavelet compression of the input signals, and a neural network prediction algorithm.

There are many applications, particularly in life-critical medical devices such as defibrillators, pace-makers, and artificial heart pumps where wires are very short (inches to a few feet), and are the least reliable component of the system. A method of testing these short wires in situ, capable of providing early prediction of failure would be of great benefit.

A system may provide predictive failure capability for life-critical wiring, connector and internal components of medical devices. This technology may be applied outside the medical field as well, for example in flight critical applications.

Figure 10:
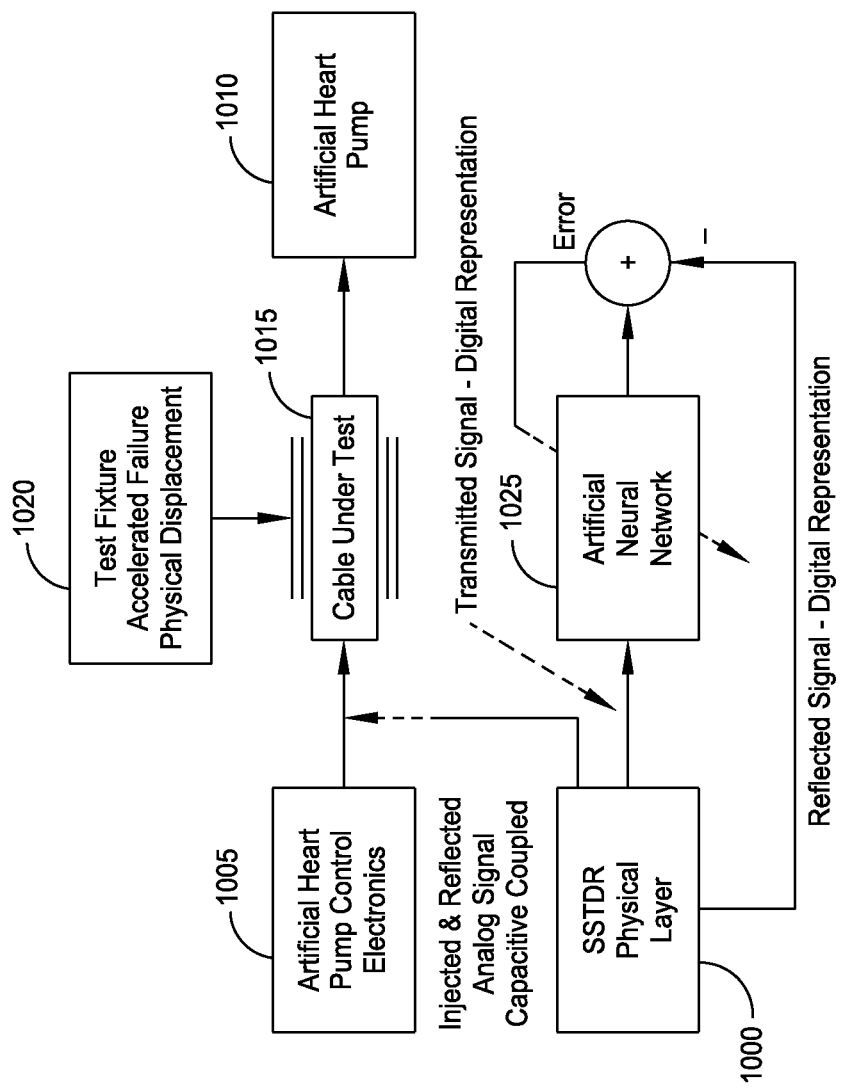
FIG. 10 illustrates a top-level system diagram of the invention, as utilized on the artificial heart system.

FIG. 10 illustrates a top-level system diagram of the invention, as utilized on the artificial heart system.

The system may include SSTDR electronics 1000, artificial heart pump control electronics 1005, an artificial heart 1010, a cable under test 1015, a text fixture 1020, and an artificial neural network 1025.

In an embodiment, SSTDR electronics 1000 are the physical layer electronics generating an analog spread spectrum signal that is injected into the wire under test, and then gathers the signal that is reflected. The physical layer 1000 is also able to generate time-domain representations of the transmitted and reflected signals in the digital domain using analog to digital converters (ND). The reflected signal is processed by a matched filter then integrated to the extent necessary to achieve a given signal to noise ratio (SNR). This block 1000 also has the ability to multiplex the injected and reflected signals to a cable that contains more than one wire. In one embodiment, this physical layer may be later integrated into the control electronics 1005 shown herein below.

Artificial heart pump control electronics 1005 are the control electronics which generate the electrical signals to drive the magnetically levitated artificial heart 1010 as well as levitation control loop, feedback circuits, communication circuits, etc.

Artificial heart 1010 may include a magnetically levitated artificial heart, a life-saving implantable medical device. In another embodiment, the component of artificial heart 1010 may be another implanted medical device or may be a non-medical device using wires.

Cable under test 1015 is a life-critical percutaneous cable that connects the implanted artificial heart to the external control electronics. In the diagram below, the electronics, cable and pump are part of a test fixture for training of the neural network.

Test fixture for accelerated failure physical displacement 1020 is an automated test fixture with the capability of physically displacing the cable assembly in such manners and with degrees of freedom that produce equivalent cable failure modes of a live patient, accelerated only in the time dimension. For implantable devices, a suitable test fixture may also include physical displacement in a submerged environment to capture failure modes caused by fluid wicking or other failures which occur in vivo in patients.

Artificial neural network 1025 may include a multi-layer feed-forward, nonlinear artificial neural network itself (ANN), as well as the transmit signal, the reflected signal, error measurement, and utilization of the error providing feedback that drives a gradient descent learning algorithm (e.g., Levinburg/Marquardt, Newton, etc.).

Artificial neural network 1025 takes as its input a digital representation of the transmitted signal, which may alternatively be a wavelet compressed representation, to lower the input dimensionality of the signal. Some details of wavelet compression are described hereinbelow.

A digital representation of the reflected signal is also provided by the SSTDR function. This function may also be advantageously wavelet compressed. Both transmitted and reflected signals must be in the same domain. An error signal is composed of the transmitted signal S, minus the reflected signal R, such that the error E is given by: E=S−R.

In this network, the transmitted and reflected signals include the time dimension. The time dimension is sampled and integrated by the SSTDR physical layer such that the time-domain signals impressed on the neural network contain Shannon information (from Shannon Information Theory) sufficient to capture the desired defect. FIG. 3 shows the equations for signal energy as well as natural reflections from expected impedance changes in the cable. It follows that reflections also hold true for any physical damage that occurs to a particular wire, at some signal to noise ratio (SNR).

In the implementation of the neural network, the network may contain and simultaneously process information from just a single conductor of interest, or from multiple conductors. This exposes failure modes that are of an inter-conductor nature in addition to single mode failures.

In an embodiment, a system is provided to sample a known-good cable, which is mechanically perturbed to failures in accelerated time. Time to failure may then be scaled from accelerated time to real-time. This allows failure prediction thresholds to be calculated for the neural network.

The neural network may be trained to recognize patterns of cables from known good new condition to any number of failure modes given sufficient training vectors. Such failure modes are automatically generated by the physical test fixture and sufficient data acquisition.

It can be shown that properly trained networks provide automatic classification of complex input data and generalize well when challenged with unseen patterns of the input space. For details, refer to "Universal Approximation Theory" at http://en.wikipedia.org/wiki/Universal_approximation_theorem, which was downloaded 3 Jun. 2010, was last modified on 27 Nov. 2009, and is hereby incorporated by reference. In addition, the following references are hereby included herein by reference:

1. Balázs Csanád Csáji. *Approximation with Artificial Neural Networks*; Faculty of Sciences; Eötvös Loránd University, Hungary 2. G. Cybenko. *Approximations by superpositions of sigmoidal functions*. Mathematics of Control, Signals, and Systems, 2:303-314, 1989.

3. Kurt Hornik: *Approximation Capabilities of Multilayer Feedforward Networks*. Neural Networks, vol. 4, 1991.

4. Haykin, Simon (1998). *Neural Networks: A Comprehensive Foundation*, 2, Prentice Hall. ISBN 0132733501.

After training, an appropriate neural network can be used to analyze and classify signal in vivo so as to provide early warning of changes in the electrical cable. Selection of the prediction time is a trade-off in classification certainty, i.e., longer integration time in the SSTDR level provides a better SNR ratio, and lower uncertainty of a prediction, which is therefore a function of time (i.e., integration time.) It is possible to characterize the performance of any particular design using normal validation methods.

Input space for the neural network is, n-space, or more formally $\mathbb{R}^n$ where n is the sampled vector size. The number of training vectors required to satisfactorily train a neural network is on the same order. Thus for systems with a large n, some method of reducing the input space dimensionality is required.

Wavelet compression is an ideal method for compressing time-domain signals as in this invention, in particular because wavelet families have been designed by various mathematicians which detect discontinuities even if such discontinuities occur at the second or higher derivative of the signal function.

Wavelet compression has the characteristic that the energy in a time-domain signal can be represented compactly (lower number of dimensions). A design criteria allows a threshold to be determined that captures a desired percentage of the given signal in a smaller space.

FIGS. 11-13 show that analysis by wavelets can detect a discontinuity in one of a signal's derivatives. The signal, while apparently a single smooth curve, is actually composed of two separate exponentials.

FIG. 11 shows the input signal which is a sum of two exponentials. It is a length of approximately 200 samples (400 through 600). FIGS. 12 and 13 show a first level wavelet decomposition as an approximation and detail level using a Daubechies (Ingrid Daubechies, Princeton University) DB4 wavelet. The details have energy only in the middle of the signal where the discontinuity appears and are small elsewhere. This indicates high frequency information is present, and moreover, this energy can be represented compactly as approximately 40 samples, consisting of 20 approximation plus 20 detail coefficients.

The Daubechies orthogonal wavelet family D2-D20, using even index number only are commonly used. Any particular wavelet has a number of vanishing moments equal to half the number of coefficients. For example D2 (the Haar wavelet) has only one vanishing moment, while D4 has two, etc. Using a D4 wavelet allows encoding a polynomial signal with two coefficients, D6 with 3, etc. Many other wavelet families have been designed with equivalent or superior performance for any particular application. Selection and use of the appropriate wavelet is a design choice. Information on wavelets is provided at http://en.wikipedia.org/wiki/Wavelets, which was downloaded on 3 Jun. 2010, was last modified on 23 May 2010, and is hereby incorporated herein by reference.

A method that eclipses prior art for spread spectrum time domain reflectometry (SSTDR) has been developed based on a unique method of constructing an up sampled PN sequence without increasing the resulting spectrum of the original sequence. A system simulation that implements the method, simulates a channel (wires) with defects has been written and tested with encouraging results.

A system level solution has been invented and described that utilizes the SSTDR method in addition to an automatic physical test fixture that stresses cables to a failure mode and to automatically generate a trained neural network solution that can predict a potential failure in advance of an actual failure. This is of extreme importance in life critical medical applications, and perhaps in other industries.

A predictive system may be built and tested on clinical percutaneous cables for the WorldHeart magnetically levitated artificial heart (LevaCor).

What is claimed is:

1. A system for determining a fault location on a wire, the system comprising:
    a (pseudo random) PN code having a chip-time;
    software code for delaying the PN code a series of delays to form delayed PN samples, a sum of the series of delays being less than one chip-time;
    software code for summing the delayed PN samples with the PN code to form a summed sequence;
    software code for transmitting the summed PN sequence to a wire being tested;
    software code for receiving a signal from the wire being tested related to the summed PN sequence;
    software code for mixing the signal received from the wire being tested with a delayed copy of the summed PN sequence so as to form a mixed signal;
    software code for integrating the mixed signal to map faults so as to detect indications of failures;

a database of known good signatures obtained from previously tested known good wires and known failure mode signatures obtained from previously tested wires with known defects: and an artificial neural network for processing the software code for integrating the mixed signal to map faults, wherein the neural network compares the map faults as a signature of the wire being tested against the database of known good signatures and failure mode signature to predict a potential failure of the wire.

2. The system of claim,1 wherein the chip-time and the software code for delaying the PN code a series of delays is configured for determining the fault location on a wire that exhibits a length of approximately 2 feet or less.

3. The system of claim 2, wherein the system is configured to determine the fault location along the wire to within approximately 1 inch or less.

4. The system of claim 1, further comprising:
software code for calculating a time to failure threshold based on a sampling of a known good wire with a predetermined defect introduced upon the known good wire; and
software code for predicting a time to failure based on the calculated time to failure threshold.

5. The system of claim 1, wherein the chip-time and the software code for delaying the PN code a series of delays is configured for determining the fault location on a wire of an artificial heart pump.

6. The system of claim 1, wherein the chip-time and the software code for delaying the PN code a series of delays is configured for determining the fault location on a wire of a pacemaker.

7. The system of claim 1, wherein the chip-time and the software code for delaying the PN code a series of delays is configured for determining the fault location on a wire of a defibrillator.

8. The system of claim 1, wherein the software code for integrating the mixed signal to map faults so as to detect indications of failures only requires access to one end of the wire being tested.

9. A method of testing a wire, the method comprising:
providing a (pseudo random) PN code having a chip-time;
delaying the PN code a series of delays to form delayed PN samples, a sum of the series of delays being less than one chip-time;
summing the delayed PN samples with the PN code to form a summed sequence;
transmitting the summed PN sequence to a wire being tested;
receiving a signal from the wire being tested related to the summed PN sequence;
mixing the signal received from the wire being tested with a delayed copy of the summed PN sequence so as to form a mixed signal;
integrating the mixed signal to map faults so as to detect indications of failures; processing the mixed signal to map faults with a neural network; and
comparing the map faults as a signature of the wire against a database of known good signatures and known failure mode signatures using the neural network.

10. The method of claim 9, further comprising determining a fault location on a wire exhibiting a length of approximately 2 feet or less using the chip-time and the software code for delaying the PN code a series of delays.

11. The method of claim 10, further comprising determining the fault location along the wire to within approximately 1 inch or less.

12. The method of claim 9, further comprising:
calculating a time to failure threshold based on a sampling of a known good wire with a predetermined defect introduced upon the known good wire; and
predicting a time to failure based on the calculated time to failure threshold.

13. The method of claim 9, further comprising determining the fault location on a wire of an artificial heart pump with the chip-time and the software code for delaying the PN code a series of delays.

14. The method of claim 9, wherein determining the fault location on a wire of a pacemaker with the chip-time and the software code for delaying the PN code a series of delays.

15. The method of claim 9, further comprising determining the fault location on a wire of a defibrillator with the chip-time and the software code for delaying the PN code a series of delays.

16. The method of claim 9, further comprising detecting indications of failures with only access to one end of the wire being tested.

* * * * *

UNITED STATES PATENT AND TRADEMARK OFFICE
CERTIFICATE OF CORRECTION

PATENT NO. : 8,706,431 B2  
APPLICATION NO. : 12/820884  
DATED : April 22, 2014  
INVENTOR(S) : W. Kurt Dobson and Gill B. Bearnson Page 1 of 1

It is certified that error appears in the above-identified patent and that said Letters Patent is hereby corrected as shown below:

In the Claims

Claim 14, line 34, please delete the word "wherein" and replace with "further comprising".

Signed and Sealed this
Eighteenth Day of August, 2015

Michelle K. Lee
*Director of the United States Patent and Trademark Office*